(12) United States Patent
Lowery et al.

(10) Patent No.: US 11,337,945 B2
(45) Date of Patent: May 24, 2022

(54) C5 KETONE COMPOSITIONS, AND RELATED METHODS, FOR THERAPEUTIC AND PERFORMANCE SUPPLEMENTATION

(71) Applicant: Keto Innovations, LLC, Melissa, TX (US)

(72) Inventors: Ryan P. Lowery, Tampa, FL (US); Shawn Wells, Frisco, TX (US); Jacob Wilson, Tampa, FL (US); Kylin Liao, Frisco, TX (US)

(73) Assignee: Keto Innovations, LLC, Melissa, TX (US)

( * ) Notice: Subject to any disclaimer, the term of this patent is extended or adjusted under 35 U.S.C. 154(b) by 0 days.

(21) Appl. No.: 16/306,412

(22) PCT Filed: Aug. 1, 2017

(86) PCT No.: PCT/IB2017/054679
§ 371 (c)(1),
(2) Date: Nov. 30, 2018

(87) PCT Pub. No.: WO2017/208217
PCT Pub. Date: Dec. 7, 2017

(65) Prior Publication Data
US 2020/0315997 A1 Oct. 8, 2020

Related U.S. Application Data

(60) Provisional application No. 62/343,941, filed on Jun. 1, 2016.

(51) Int. Cl.
*A61K 31/19* (2006.01)
*A61P 3/08* (2006.01)

(52) U.S. Cl.
CPC ............... *A61K 31/19* (2013.01); *A61P 3/08* (2018.01)

(58) Field of Classification Search
CPC ...... A61K 31/19; C07C 53/124; C07C 53/126
USPC .................. 514/578; 562/508, 579
See application file for complete search history.

(56) References Cited

U.S. PATENT DOCUMENTS

| 6,380,244 | B2 | 4/2002 | Martin et al. |
| 6,613,356 | B1 | 9/2003 | Vlahakos |
| 9,675,577 | B2 | 6/2017 | D'Agostino |
| 2011/0306663 | A1 | 12/2011 | Schiffmann et al. |
| 2014/0221482 | A1 | 8/2014 | Mochel et al. |
| 2017/0296501 | A1 | 10/2017 | Lowery et al. |

FOREIGN PATENT DOCUMENTS

WO   2015073803 A1   5/2015

OTHER PUBLICATIONS https://www.merriam-webster.com/dictionary/isoform; last accessed Sep. 24, 2021. (Year: 2021).*
International Search Report for International Application No. PCT/IB2017/054679 "C5 Ketone Compositions, and Related Methods, for Therapeutic and Performance Supplementation" dated Jan. 9, 2018.
Written Opinion for International Application No. PCT/IB2017/054679 "C5 Ketone Compositions, and Related Methods, for Therapeutic and Performance Supplementation" date of completion is Dec. 16, 2017.
International Preliminary Report on Patentability for International Application No. PCT/IB2017/054679 "C5 Ketone Compositions, and Related Methods, for Therapeutic and Performance Supplementation" dated Dec. 4, 2018.
Roe, CR., et al., Carnitine Palmiloytransferase II Deficiency Successful Anaplerotic Diet Therapy, Neurology 2008, vol. 71, pp. 260-264.
Ardawi and Newsholme, "Maximum activities of some enzymes of glycolysis, the tricarboxylic acid cycle and ketone-body and glutamine utilization pathways in lymphocytes of the rat", Biochem J (1982) 208(3): 743-748.
Mochel, F., et al., "Pyruvate carboxylase deficiency: clinical and biochemical response to anaplerotic diet therapy", Molecular Benetics and Metabolism, 2005, 84(4): 305-312.
Roe, C.R., Mochel, F. Anaplerotic diet therapy in inherited metabolic disease: Therapeutic potential J Inherit Metab Dis 29, 332-340 (2006).

* cited by examiner

*Primary Examiner* — Jeffrey H Murray
(74) *Attorney, Agent, or Firm* — Ferguson Braswell Fraser Kubasta PC (57) ABSTRACT

The present disclosure pertains to compositions and methods for the treatment and/or prevention of one or more of obesity, diabetes, metabolic syndrome, Alzheimer's disease, Chronic Fatigue Syndrome (CFS), aging, fibromyalgia, dyslipidemia, hypercholesterolemia, dyslipidemia, Parkinson's disease, migraines, Traumatic Brain Injury (TBI), Attention Deficit Disorder (ADD)/Attention Deficit Hyperactivity Disorder (ADHD), Cancer, Cardiovascular Disease (CVD)/Coronary Artery Disease (CAD), Chronic Pain, neuralgia, depression, amyotrophic lateral sclerosis (ALS), and epilepsy, Insufficient Cellular Energy (ICE) and mitochondrial dysfunction. The present disclosure also pertains to methods for increasing mental and/or physical performance levels and/or decreasing exertion during exercise in a subject by the administration of C5 ketones.

20 Claims, 6 Drawing Sheets

C5 KETONE COMPOSITIONS, AND RELATED METHODS, FOR THERAPEUTIC AND PERFORMANCE SUPPLEMENTATION

RELATED APPLICATIONS

This application is the U.S. National Stage of International Application No. PCT/IB2017/054679, filed Aug. 1, 2017, which designates the U.S., published in English, and claims the benefit of U.S. Provisional Application No. 62/343,941, filed Jun. 1, 2016. The entire teachings of the above applications are incorporated herein by reference.

BACKGROUND

β-hydroxybutyrate (BHB) (a C4 ketone) and its salts, esters, and combinations thereof have become increasingly common in the marketplace for the ability to increase blood BHB levels, promote increases in cognitive function, and an array of benefits that may benefit diseased individuals.

The heart, brain and kidney are the three organs with the highest activity of enzymes utilizing ketone bodies (Ardawi and Newsholme, *Biochem J* 208(3): 743-748, 1982). For instance, studies have shown an improvement in the neurological status of a newborn with pyruvate carboxylase deficiency during treatment with triheptanoin (C7 ketone) (Mochel, F., et al., *Molecular Genetics and Metabolism* 84(4):305-312, 2005; Roe and Mochel *J Inherit Metab Dis* 29, 332-340, 2006).

BRIEF SUMMARY

In one aspect, the subject disclosure provides methods for increasing mental and/or physical performance levels in a subject, the methods comprising administering to the subject a therapeutically effective amount of a C5-ketone body, or pharmaceutically acceptable salt, ester, or chelate thereof. In some embodiments, the methods described aid Kreb cycle function and/or anaplerosis in a subject being treated with the described compositions. In some embodiments of this aspect, the C5-ketone body is β-ketopentanoate.

In some embodiments, the mental performance level being increased is a measure of well-being and/or focus.

In some embodiments, the physical performance level being increased is energy.

In another aspect, the subject disclosure provides methods for increasing blood ketone levels in a subject, the methods comprising administering to the subject a therapeutically effective amount of a C5-ketone body, or pharmaceutically acceptable salt, ester, or chelate thereof. In some embodiments of this aspect, the C5-ketone body is β-hydroxypentanoate.

In another aspect, the subject disclosure provides methods for treating and/or preventing one or more of obesity, diabetes, metabolic syndrome, Alzheimer's disease, Chronic Fatigue Syndrome (CFS), aging, fibromyalgia, dyslipidemia, hypercholesterolemia, dyslipidemia, Parkinson's disease, migraines, Traumatic Brain Injury (TBI), Attention Deficit Disorder (ADD)/Attention Deficit Hyperactivity Disorder (ADHD), Cancer, Cardiovascular Disease (CVD)/Coronary Artery Disease (CAD), Chronic Pain, neuralgia, depression, amyotrophic lateral sclerosis (ALS), epilepsy, Insufficient Cellular Energy (ICE) and mitochondrial dysfunction in a subject, the methods comprising administering to the subject a therapeutically effective amount of a C5-ketone body, or pharmaceutically acceptable salt, ester, or chelate thereof.

In yet another aspect, the subject disclosure provides methods for decreasing blood glucose levels and/or increasing BHB levels in a subject, the methods comprising administering to the subject a therapeutically effective amount of a C5-ketone body, or pharmaceutically acceptable salt, ester, or chelate thereof. In some embodiments of this aspect, the C5-ketone body is β-ketopentanoate.

In yet another aspect, the subject disclosure provides methods for aiding in weight loss in a subject, the methods comprising administering to the subject a therapeutically effective amount of a C5-ketone body, or pharmaceutically acceptable salt, ester, or chelate thereof.

In another aspect, the subject disclosure provides methods for lowering exertion during exercise in a subject, the methods comprising administering to the subject a therapeutically effective amount of a C5-ketone body, or pharmaceutically acceptable salt, ester, or chelate thereof.

In a further aspect, the subject disclosure provides compositions comprising a therapeutically effective amount of C5-ketone body, or pharmaceutically acceptable salt, ester, or chelate thereof. The compositions may be for the treatment of the diseases and conditions described herein. In some embodiments, the compositions further include an acceptable carrier. In some embodiments, the C5-ketone body, or pharmaceutically acceptable salt, ester, or chelate thereof, concentration is from about 1 gram to about 50 grams.

DETAILED DISCLOSURE

The present disclosure pertains to compositions and methods for the treatment and/or prevention of one or more of obesity; diabetes; metabolic syndrome; Alzheimer's disease; Chronic Fatigue Syndrome (CFS); aging; fibromyalgia; dyslipidemia; hypercholesterolemia; dyslipidemia; Parkinson's disease; migraines; Traumatic Brain Injury (TBI); Attention Deficit Disorder (ADD)/Attention Deficit Hyperactivity Disorder (ADHD); Cancer, such as for example, glioblastoma; Cardiovascular Disease (CVD)/Coronary Artery Disease (CAD); Chronic Pain; neuralgia; depression; amyotrophic lateral sclerosis (ALS); epilepsy; Insufficient Cellular Energy (ICE) and mitochondrial dysfunction. The present disclosure also pertains to methods for increasing mental and/or physical performance levels.

There are many potential forms of C5 ketones. C5 ketones could be unbound in their "free acid" state; or C5 ketones can be salts (e.g. sodium, calcium, magnesium, etc.), esters (e.g. glycerol), chelates (e.g. amino acids), or any other chemical variant with C5 ketones attached. Further, C5 ketones can be in combination with other compounds, including other carbon length ketones themselves.

Two C5 ketones are β-hydroxypentanoate (BHP) [R, S, & RS isoforms] and β-ketopentanoate (BKP) (also known as 3-hydroxyvalerate and 3-ketovalerate). These C5 ketones are homologues of physiological ketone bodies, β-hydroxybutyrate (BHB) and acetoacetate. C5 ketone bodies are naturally formed in the liver from the partial oxidation of odd chain fatty acids (e.g. C-7, heaptanoic acid, like macadamia nut oil). C5 ketones have been shown to occur in trace amounts in human plasma and most plants. They are derived from the oxidation in liver of the R-moiety of R,S-1,3-pentanediol, a potential nutrient. Whether administered by bolus or constant infusion, the two substrates are interconverted and rapidly metabolized in an animal model.

Researchers found at least during short-term experiments, β-hydroxypentanoate (BHP) and β-ketopentanoate (BKP) are well metabolized in animals without apparent intolerance to a large supply of propionyl-CoA. In nondiabetic animals, C5-ketone bodies ((R)-3-hydroxypentanoate and 3-ketopentanoate) are very rapidly used when administered intravenously at doses corresponding to 75% of the energy requirement (Leclerc et al 1995).

Like their C4 counterparts, the C5 ketone bodies are interconverted by mitochondrial BHB dehydrogenase. In peripheral tissues, C5 ketone bodies are converted to propionyl-CoA (which is anaplerotic). Peripheral tissues have a high capacity to utilize exogenous C5 ketone bodies, especially heart, kidney, and brain, which have high activities of 3-oxoacid-CoA transferase. As shown in the present disclosure, C5 ketone bodies provide a unique benefit in promoting increases in mental and physical performance, aiding Kreb cycle function, and contributing as a unique aide in various diseased populations (e.g. obesity, diabetes, cancer, cardiovascular disease, epilepsy, Alzheimer's, Parkinson's, etc.) and anaplerotic scenarios. C5 ketone bodies also aid in weight loss/fat loss.

Several aspects of the disclosure are described below, with reference to examples for illustrative purposes only. It should be understood that numerous specific details, relationships, and methods are set forth to provide a full understanding of the disclosure. One having ordinary skill in the relevant art, however, will readily recognize that the aspects described can be practiced without one or more of the specific details or practiced with other methods, protocols, reagents, and animals. The aspects described are not limited by the illustrated ordering of acts or events, as some acts may occur in different orders and/or concurrently with other acts or events. Furthermore, not all illustrated acts, steps or events are required to implement a methodology in accordance with the aspects described. Many of the techniques and procedures described, or referenced herein, are well understood and commonly employed using conventional methodology by those skilled in the art.

Prior to setting forth aspects of the disclosure in detail, it may be helpful to the understanding thereof to define several terms, and these are accordingly set forth in the next section, below. Unless otherwise defined, all terms of art, notations and other scientific terms or terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly used dictionaries, should be interpreted as having a meaning that is consistent with their meaning in the context of the relevant art and/or as otherwise defined herein.

The terminology used herein is for the purpose of describing particular embodiments only and is not intended to be limiting. As used herein, the indefinite articles "a", "an" and "the" should be understood to include plural reference unless the context clearly indicates otherwise.

The phrase "and/or," as used herein, should be understood to mean "either or both" of the elements so conjoined, i.e., elements that are conjunctively present in some cases and disjunctively present in other cases.

As used herein, "or" should be understood to have the same meaning as defined above for "and/or". For example, when separating a listing of items, "and/or" or "or" shall be interpreted as being inclusive, i.e., the inclusion of at least one, but also including more than one, of a number of items, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

As used herein, the terms "including", "includes", "having", "has", "with", or variants thereof, are intended to be inclusive similar to the term "comprising."

As used herein, the term "subject" refers to an animal. Typically, the terms "subject" and "patient" may be used interchangeably herein in reference to a subject. As such, a "subject" includes an animal that is being treated for conditions described in the present disclosure, such as, but not limited to, obesity, diabetes, metabolic syndrome, Alzheimer's disease, Chronic Fatigue Syndrome (CFS), aging, fibromyalgia, dyslipidemia, hypercholesterolemia, dyslipidemia, Parkinson's disease, migraines, Traumatic Brain Injury (TBI), Attention Deficit Disorder (ADD)/Attention Deficit Hyperactivity Disorder (ADHD), Cancer, Cardiovascular Disease (CVD)/Coronary Artery Disease (CAD), Chronic Pain, neuralgia, depression, amyotrophic lateral sclerosis (ALS), and epilepsy, Insufficient Cellular Energy (ICE) and mitochondrial dysfunction; or the recipient of a mixture of components or compositions as described herein. The term "animal," includes, but is not limited to, a mammal, such as a mouse, rat, dog, guinea pig, cow, horse, chicken, cat, rabbit, pig, monkey, chimpanzee, and human.

The term "effective amount" or "therapeutically effective amount" means that amount of active compound that elicits the biological or medicinal response in a tissue system, animal or human that is being sought by a researcher, veterinarian, medical doctor or other clinician, which includes alleviation of one or more of the symptoms of the disease or disorder being treated; reduction of the severity of one or more of the symptoms of the disease or disorder being treated; or otherwise provides the desired effect. The precise dosage will vary according to a variety of factors such as subject-dependent variables (e.g., age, medical history, etc.), the disorder or condition, and the treatment being affected.

In particular aspects of the present disclosure directed to co-therapy or combination therapy, comprising administration of a therapeutically effective amount of a C5-ketone body, or pharmaceutically acceptable salt, ester, or chelate thereof, and other carbon length ketones, therapeutically effective amount means that amount of the combination of agents taken together so that the combined effect elicits the desired biological or medicinal response. For example, the therapeutically effective amount of co-therapy comprising administration of a C5-ketone body, or pharmaceutically acceptable salt, ester, or chelate thereof, and other carbon length ketones would be the amount of the C5-ketone body and the amount of the other carbon length ketone(s) that, when taken together or sequentially, have a combined effect that is therapeutically effective. Further, it will be recognized by one skilled in the art that in the case of co-therapy with a therapeutically effective amount, as in the example above, the amount of C5-ketone body, or pharmaceutically acceptable salt, ester, or chelate thereof, and other carbon length ketone, individually, may or may not be therapeutically effective.

The term "pharmaceutically acceptable," as used herein, means approved by a regulatory agency of the Federal or a state government or listed in the U.S. Pharmacopeia or other generally recognized pharmacopeia for use in animals and/or in humans.

"Pharmaceutically acceptable salt" refers to a salt of a compound of the disclosure that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2naphthalenesulfonic acid, 4-toluenesulfonic acid, camphorsulfonic acid, 4-methylbicyclo [2.2.2]-oct-2-ene-1-carboxylic acid, glucoheptonic acid, 3-phenylpropionic acid, trimethylacetic acid, tiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced.

Aspects of the present disclosure provide compositions comprising one or more C5-ketone body, or pharmaceutically acceptable salt, ester, or chelate thereof, as the active ingredient. The compositions described can also be in the form of a pharmaceutical composition comprising one or more pharmaceutically acceptable carriers described herein. The compounds and compositions of the disclosure can be used to treat, alleviate, inhibit or prevent the diseases and conditions further described herein. Further, the compounds and compositions of the disclosure can be used for increasing mental and/or physical performance levels in a subject or for aiding in weight loss. In some embodiments, the C5 ketone body, or pharmaceutically acceptable salt, ester, or chelate thereof, concentration is from about 1 gram to about 50 grams. In some embodiments, the C5-ketone, or pharmaceutically acceptable salt, ester, or chelate thereof, concentration is from about 1 gram to about 40 grams. In some embodiments, the C5-ketone, or pharmaceutically acceptable salt, ester, or chelate thereof, concentration is from about 1 gram to about 30 grams. In some embodiments, the C5-ketone, or pharmaceutically acceptable salt, ester, or chelate thereof, concentration is from about 1 gram to about 20 grams. In some embodiments, the C5-ketone, or pharmaceutically acceptable salt, ester, or chelate thereof, concentration is from about 1 gram to about 10 grams. In some embodiments, the C5-ketone, or pharmaceutically acceptable salt, ester, or chelate thereof, concentration is from about 10 grams to about 50 grams. In some embodiments, the C5-ketone, or pharmaceutically acceptable salt, ester, or chelate thereof, concentration is from about 20 grams to about 50 grams. In some embodiments, the C5-ketone, or pharmaceutically acceptable salt, ester, or chelate thereof, concentration is from about 30 grams to about 50 grams. In some embodiments, the C5-ketone, or pharmaceutically acceptable salt, ester, or chelate thereof, concentration is from about 40 grams to about 50 grams. In some embodiments, the C5-ketone, or pharmaceutically acceptable salt, ester, or chelate thereof, concentration is about 10 grams.

The term "carrier" refers to a diluent, adjuvant, excipient, and/or vehicle with which the compositions are administered. Such pharmaceutical carriers can be sterile liquids, such as water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. Suitable pharmaceutical excipients include starch, glucose, sucrose, gelatin, lactose, malt, rice, flour, chalk, silica gel, sodium stearate, glycerol monostearate, talc, sodium chloride, glycerol, propylene, glycol, water, ethanol and the like. The pharmaceutical composition(s) may also contain wetting or emulsifying agents or suspending/diluting agents, or pH buffering agents, or agents for modifying or maintaining the rate of release of the formulations. The compositions can take the form of solutions, suspensions, emulsion, tablets, pills, capsules, powders, gels, creams, sustained-release formulations and the like. Formulations can include standard carriers such as pharmaceutical grades of mannitol, lactose, sodium saccharine, starch, magnesium stearate, cellulose, magnesium carbonate, etc. Such compositions will contain an effective amount of the active ingredient(s) together with a suitable amount of carrier so as to provide the proper form to the subject based on the mode of administration to be used.

If for intravenous administration, the compositions are packaged in solutions of sterile isotonic aqueous buffer. Where necessary, the composition may also include a solubilizing agent. The components of the composition are supplied either separately or mixed together in unit dosage form, for example, as a dry lyophilized powder or concentrated solution in a hermetically sealed container such as an ampoule or sachet indicating the amount of active agents. If the composition is to be administered by infusion, it can be dispensed with an infusion bottle containing sterile pharmaceutical grade water or saline. Where the composition is administered by injection, an ampoule of sterile water or saline can be provided so that the ingredients may be mixed prior to injection.

Moreover, if a packaging material is utilized to package the composition, it may be biologically inert or lack bioactivity, such as plastic polymers, silicone, etc. and may be processed internally by the subject without affecting the effectiveness of the components packaged and/or delivered therewith. Additionally, the compositions and components may be packaged with additional agents.

The C5-ketones utilized in the methods and compositions may be provided in an isolated or purified form. Further, synthetic variants of the C5-ketones may be utilized, either individually or in combination with other synthetic C5-ketone variants, or in combination with non-synthetic variants.

Aspects of the present disclosure also provide kits comprising one or more C5-ketone or pharmaceutically acceptable salt, ester, or chelate thereof, as described herein. The kits may further be used in the methods described herein. The kits may also include at least one reagent and/or instructions for their use. Also, the kit may include one or more containers filled with reagent(s) and/or one or more components of the disclosure. One or more container of the kits provided may also comprise a C5-ketone, preferably in a purified form. Also, one or more container of the kits provided may also comprise another carbon length ketone, preferably in a purified form. In some embodiments, the various C5-ketones and other carbon length ketones may be provided in separate containers for mixing prior to use, or for individual ingestion/administration. The kits may also comprise a control composition, such as reagents that lack a ketone for use as a control reagent in experimentation. As it would be understood by those skilled in the art, detection or labeling methodologies can be used in the kits provided when utilized in an experimental or laboratory setting.

Aspects of the present disclosure are further directed to methods for the treatment and/or prevention of one or more of obesity, diabetes, metabolic syndrome, Alzheimer's disease, Chronic Fatigue Syndrome (CFS), aging, fibromyalgia, dyslipidemia, hypercholesterolemia, dyslipidemia, Parkinson's disease, migraines, Traumatic Brain Injury (TBI), Attention Deficit Disorder (ADD)/Attention Deficit Hyperactivity Disorder (ADHD), Cancer, Cardiovascular Disease (CVD)/Coronary Artery Disease (CAD), Chronic Pain, neuralgia, depression, amyotrophic lateral sclerosis (ALS), and epilepsy, Insufficient Cellular Energy (ICE) and mitochondrial dysfunction, which involve administering a therapeutically effective amount of a C5-ketone body, or pharmaceutically acceptable salt, ester, or chelate thereof, or pharmaceutical compositions of the present disclosure, to a subject, preferably a mammal, and most preferably a human.

C5-ketones have potential to work directly on the mitochondria, therefore, in some embodiments, the C5-ketones and related methods described by this disclosure are useful for treating mitochondrial dysfunction. As such, C5-ketones are particularly useful in treating cancers that result from mitochondrial dysfunction, such as, for example, glioblastoma.

Aspects of the present disclosure may also be directed to methods for increasing blood ketone levels in a subject, comprising administering to the subject a therapeutically effective amount of a C5-ketone body, or pharmaceutically acceptable salt, ester, or chelate thereof, such as, for example, β-hydroxypentanoate (BHP).

A further aspect of the present disclosure may be directed to methods for decreasing blood glucose levels in a subject, comprising administering to the subject a therapeutically effective amount of a C5-ketone body, or pharmaceutically acceptable salt, ester, or chelate thereof, such as, for example, β-ketopentanoate (BKP).

Aspects of the present disclosure are also directed to methods for increasing mental and/or physical performance levels which involve administering a therapeutically effective amount of a C5-ketone body, or pharmaceutically acceptable salt, ester, or chelate thereof, or pharmaceutical compositions of the present disclosure, to a subject, preferably a mammal, and most preferably a human. In some embodiments, the C5-ketone body is β-ketopentanoate. The mental performance level being increased may be a measure of well-being and/or focus. The physical performance level being increased may be a measure of energy.

In yet another aspect, the subject disclosure provides methods for aiding in weight loss in a subject, the methods comprising administering to the subject a therapeutically effective amount of a C5-ketone body, or pharmaceutically acceptable salt, ester, or chelate thereof.

In a further aspect, the subject disclosure provides methods for lowering exertion during exercise in a subject, the methods comprising administering to the subject a therapeutically effective amount of a C5-ketone body (e.g., β-ketopentanoate), or pharmaceutically acceptable salt, ester, or chelate thereof. In some embodiments, the exercise is moderate intensity exercise and in other embodiments, the exercise is high intensity exercise. Moderate intensity exercise includes, for example, running, cycling, rowing, circuit training, and yogo. High intensity exercise includes, for example, sprinting, hockey, soccer, baseball, football, basketball, resistance training and boxing.

In some embodiments, the C5-ketone, or pharmaceutically acceptable salt, ester, or chelate thereof, concentration utilized in the methods described is from about 1 gram to about 50 grams. In some embodiments, the C5-ketone, or pharmaceutically acceptable salt, ester, or chelate thereof, concentration utilized in the methods described is from about 1 gram to about 40 grams. In some embodiments, the C5-ketone, or pharmaceutically acceptable salt, ester, or chelate thereof, concentration utilized in the methods described is from about 1 gram to about 30 grams. In some embodiments, the C5-ketone, or pharmaceutically acceptable salt, ester, or chelate thereof, concentration utilized in the methods described is from about 1 gram to about 20 grams. In some embodiments, the C5-ketone, or pharmaceutically acceptable salt, ester, or chelate thereof, concentration utilized in the methods described is from about 1 gram to about 10 grams. In some embodiments, the C5-ketone, or pharmaceutically acceptable salt, ester, or chelate thereof, concentration utilized in the methods described is from about 10 grams to about 50 grams. In some embodiments, the C5-ketone, or pharmaceutically acceptable salt, ester, or chelate thereof, concentration utilized in the methods described is from about 20 grams to about 50 grams. In some embodiments, the C5-ketone, or pharmaceutically acceptable salt, ester, or chelate thereof, concentration utilized in the methods described is from about 30 grams to about 50 grams. In some embodiments, the C5-ketone, or pharmaceutically acceptable salt, ester, or chelate thereof, concentration utilized in the methods described is from about 40 grams to about 50 grams. In some embodiments, the C5-ketone, or pharmaceutically acceptable salt, ester, or chelate thereof, concentration utilized in the methods described is about 10 grams.

"Preventing" or "prevention" refers to a reduction in risk of acquiring disorder (i.e., causing at least one of the clinical symptoms of the disease/disorder not to develop in a subject that may be predisposed to the disorder but does not yet experience or display symptoms of the disorder).

"Treating" or "treatment" of any disorder refers, in one embodiment, to ameliorating the disorder (i.e., arresting or reducing the development of the disorder (e.g., Alzheimer's disease) or at least one of the clinical symptoms thereof). In another embodiment "treating" or "treatment" refers to ameliorating at least one physical parameter, which may not be discernible by the subject. In yet another embodiment, "treating" or "treatment" refers to modulating the disorder, either physically, (e.g., stabilization of a discernible symptom), physiologically, (e.g., stabilization of a physical parameter), or both. In yet another embodiment, "treating" or "treatment" refers to delaying the onset of the disorder.

Administration can be locally (confined to an area of body) and/or systemically in the subject. It may be desirable to administer the C5-ketones, or pharmaceutical compositions comprising same, locally to the area in need of treatment. This method of administration may be achieved by, for example, and not by way of limitation, local infusion, topical application, by injection, by catheter, or by means of an implant (e.g., a porous membrane). Administration may also be orally, such as but not limited to, by way of pills, capsules, liquid, vapors, or powders.

It is also understood and contemplated that aspects of this disclosure can provide more than two active ingredient components in the mixtures of compositions herein disclosed. Also, the disclosed methods can comprise the simultaneous or separate administration of multiple active ingredients. Thus, embodiments may further include the administration of a third, fourth, etc. active ingredient, wherein the third, fourth, etc. active ingredient is administered separately, but at the same time as the other active ingredients, or hours or days after the first administration of active ingredients.

In some embodiments, the C5-ketones, or pharmaceutical composition containing them, can be delivered in a controlled release system. Such methods may include the use of a pump for administration (e.g., use of an intravenous drip).

The compounds and compositions of the invention may also be utilized in pharmaceutically acceptable compositions in the methods provided herein.

It would also be understood by a skilled artisan how to use the compositions described herein for therapeutic purposes without undue experimentation based on the teachings provided throughout the specification.

The amount of active ingredients or pharmaceutical compounds of the invention which will be effective in the treatment, inhibition and/or prevention of the diseases and/or conditions described herein can be determined by standard clinical techniques. Additionally, in vitro assays may be employed to help identify optimal dosage ranges. The precise dose to be utilized will also depend on the route of administration, and the seriousness of the disease or condition, and should also be decided according to the sound medical judgment of the clinician and each patient's individual circumstances. The specific therapeutically effective dosage level for any particular patient will depend upon a variety of factors including: the type and degree of the response to be achieved; the specific composition and other agent(s), if any, employed; the age, weight, general health, sex and diet of the patient; the time of administration, route of administration, and rate of excretion of the composition; the duration of the treatment; other drugs used in combination or coincidental with the composition; and any other factors well known in the medical arts. Effective dosages may also be extrapolated from dose-response curves derived from in vitro or animal model testing systems.

Without further elaboration, it is believed that one skilled in the art can, using the preceding description, utilize the present invention to its fullest extent. The following examples are offered by way of illustration, not by way of limitation. While specific examples have been provided, the above description is illustrative and not restrictive. Anyone or more of the features of the previously described embodiments can be combined in any manner with one or more features of any other embodiments in the present invention.

Furthermore, many variations of the invention will become apparent to those skilled in the art upon review of the specification.

All publications and patent documents cited in this application are incorporated by reference in pertinent part for all purposes to the same extent as if each individual publication or patent document were so individually denoted. By citation of various references in this document, Applicants do not admit any particular reference is "prior art" to their invention.

EXAMPLES

The methods, compounds, and compositions herein described are further illustrated in the following examples, which are provided by way of illustration and are not intended to be limiting. It will be appreciated that variations in proportions and alternatives in elements of the components shown will be apparent to those skilled in the art and are within the scope of embodiments of the present invention. Theoretical aspects are presented with the understanding that Applicant does not seek to be bound by the theory presented. All parts or amounts, unless otherwise specified, are by weight.

Example 1: BHP and BKP Effects on Subject Blood Glucose and Ketone Levels; and Subject Well-being, Energy and Focus Two (2) healthy, male subjects reported to the laboratory following a 12 hour overnight fast. Subjects were instructed to randomly consume either 10 grams of BHP or 10 grams BKP dissolved in 12 ounces of water. Subjects were then monitored for 150 minutes following drinking the mixture. Blood glucose, ketones, and visual analog scales (VAS) of well-being, energy, and focus were taken at 0, 30, 60, 90, 120, and 150 minutes. VAS scales consisted of a continuum of numbers from 1-10 with 1 being extremely low and 10 being extremely high.

Blood ketones were measured via finger prick using an Abbott Precision device which determines mMol of BHB. Blood glucose was measures using Abbott Precision glucose strips and was measured in mg/dL.

Figure 1:
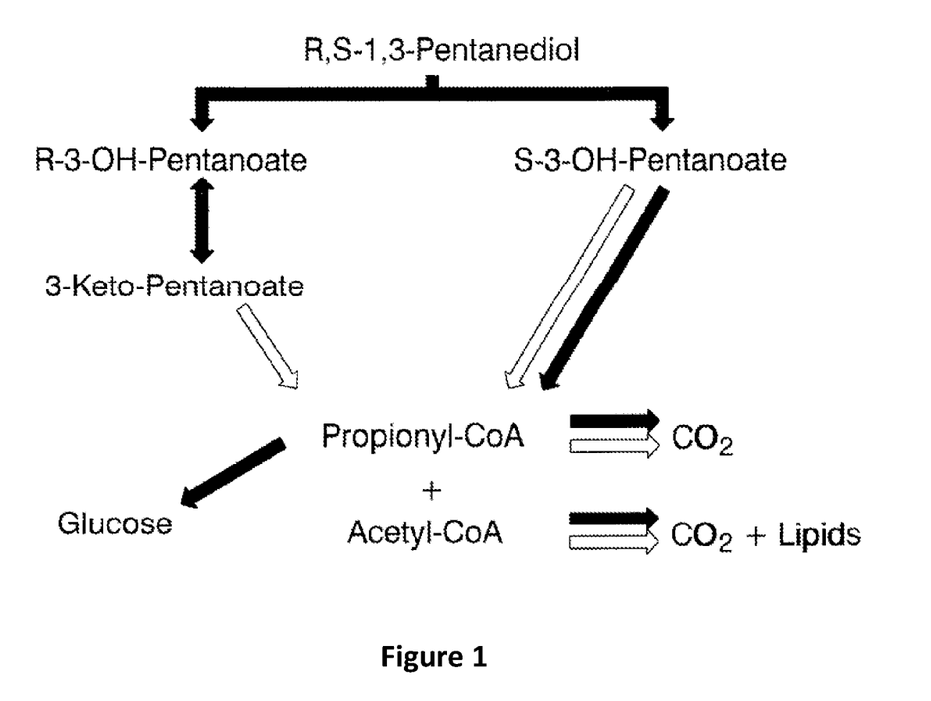
FIG. 1 illustrates the metabolism of C5 ketones in their racemic mixture and dissociated into their respective isoforms.
Figure 2:
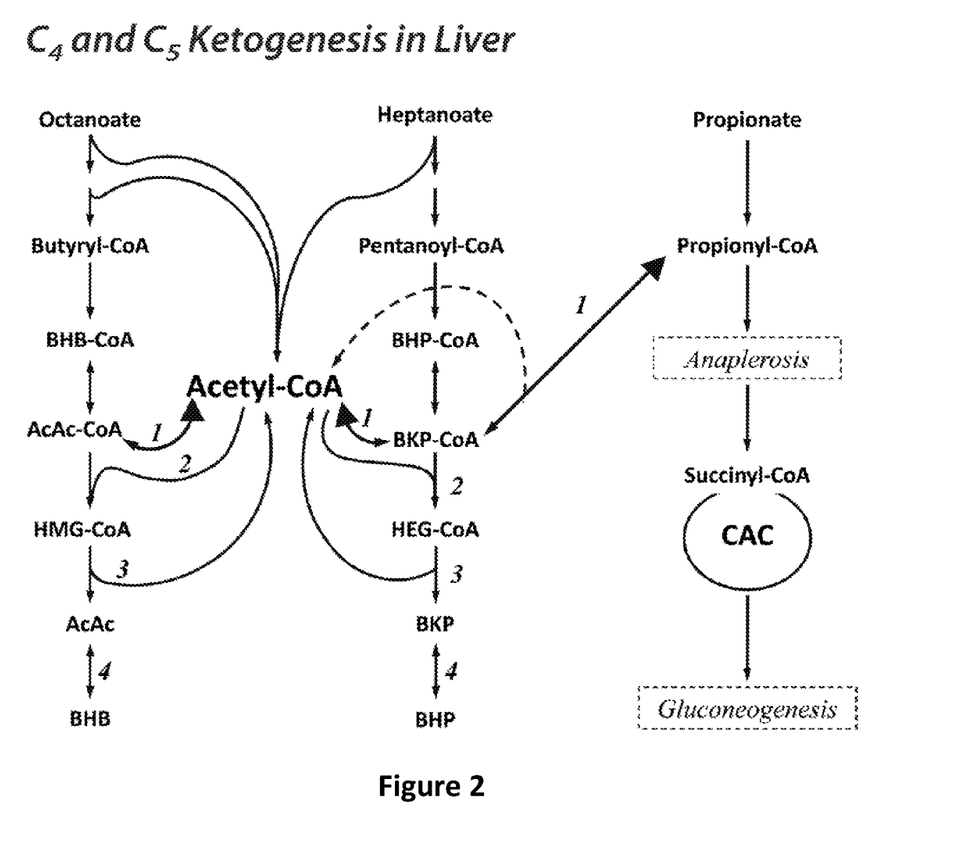
FIG. 2 illustrates C4 ketogenesis and C5 ketogenesis in the liver. Numbers refer to the following enzymes: 3-ketoacyl-CoA thiolase (1); HMG-CoA synthase (2); HMG-CoA lyase (3); and β-hydroxybutyrate dehydrogenase (4). The figure also shows the link between propionyl-CoA and the CAC via anaplerosis.
Figure 3:
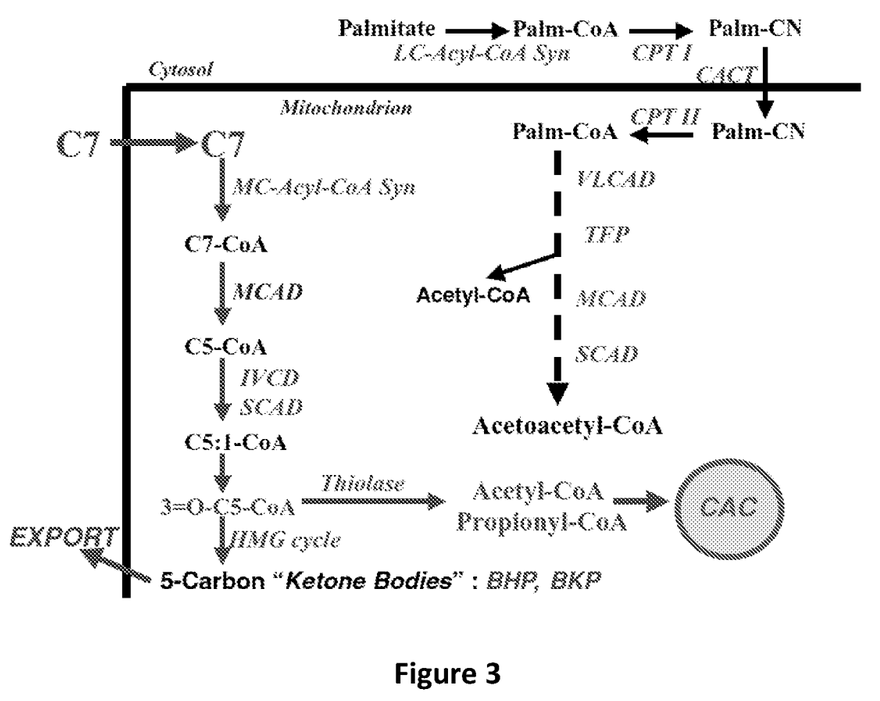
FIG. 3 illustrates the metabolism of triheptanoin into C5 ketone bodies BHP and BKP, which ultimately get transported out of the mitochondria.
Figure 4:
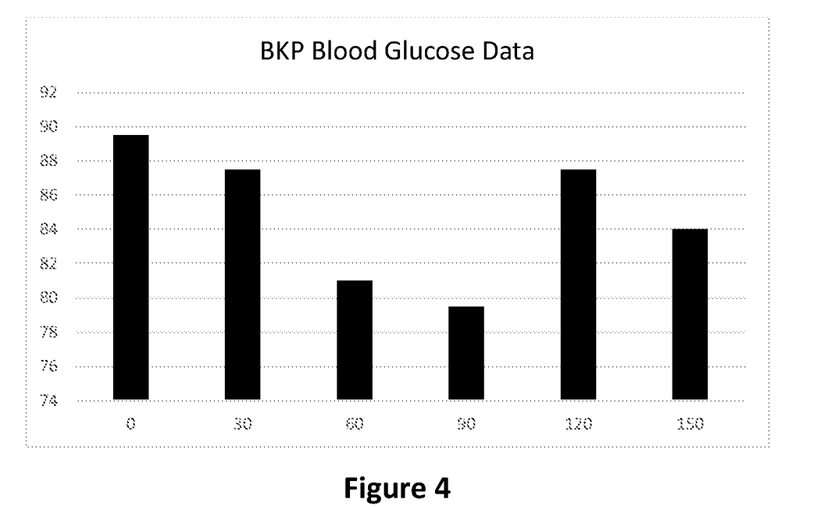
FIG. 4 shows a graph of blood glucose level with BKP administration.
Figure 5:
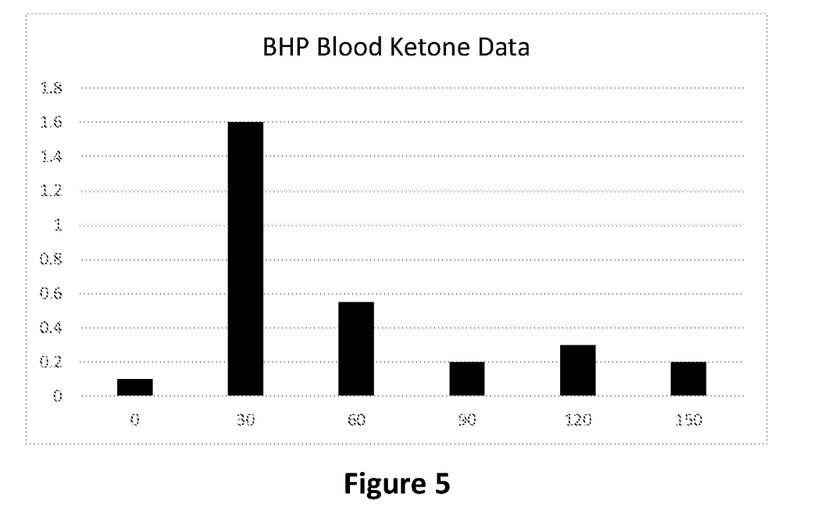
FIG. 5 shows a graph of blood ketone level with BHP administration.
Figure 6:
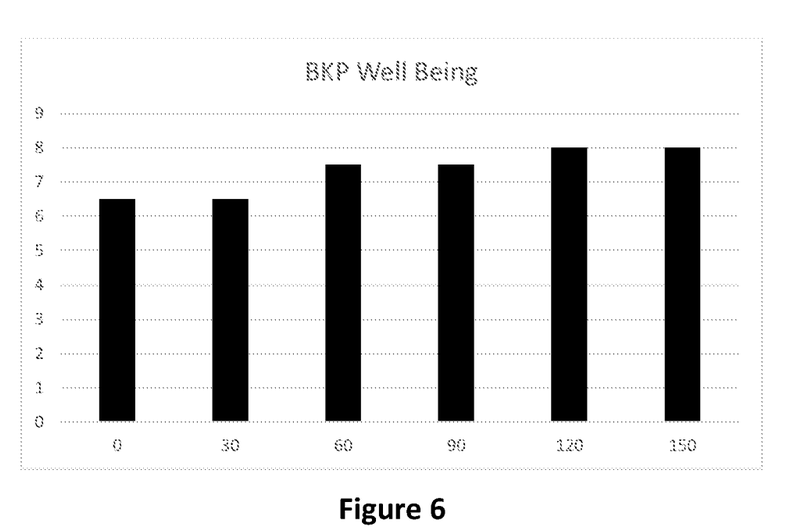
FIG. 6 shows a graph of visual analog scales (VAS) of well-being with BKP administration.
Figure 7:
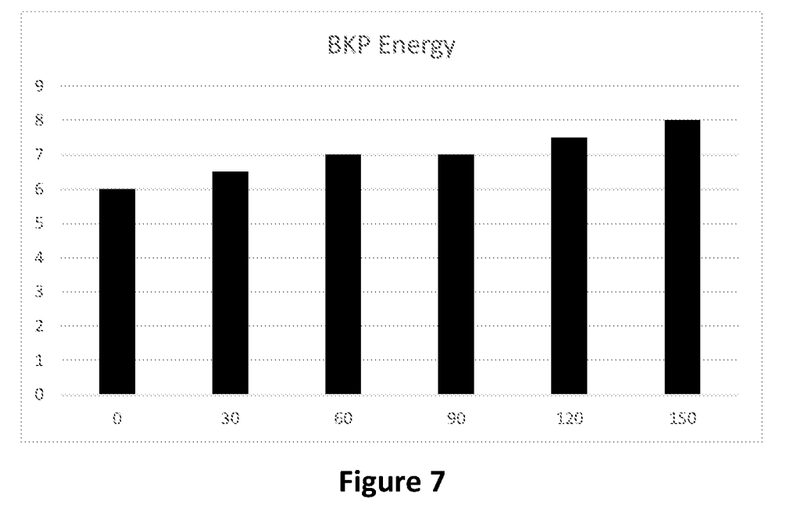
FIG. 7 shows a graph of VAS of energy with BKP administration.
Figure 8:
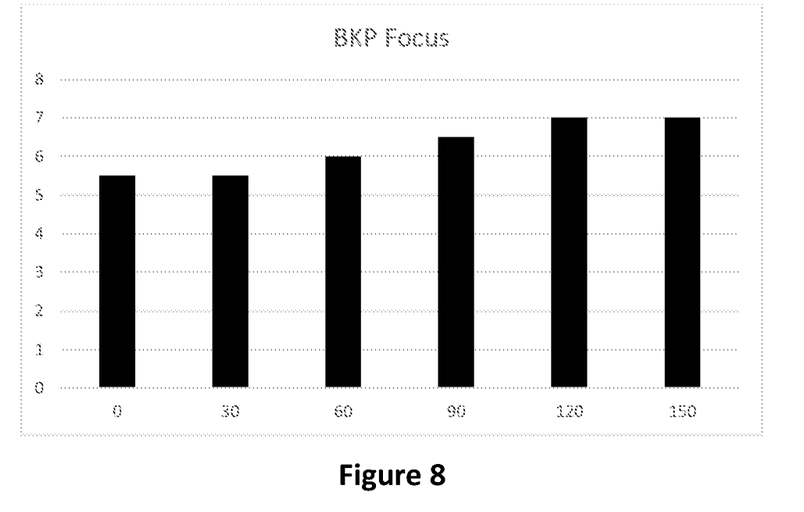
FIG. 8 shows a graph of VAS of focus with BKP administration.

Results are summarized in Table 1 and FIG. 4 (FIG. 4 shows a graph of blood glucose level with BKP administration), Table 2 and FIG. 5 (FIG. 5 shows a graph of blood ketone level with BHP administration), Table 3 and FIG. 6 (FIG. 6 shows a graph of VAS of well-being with BKP administration), Table 4 and FIG. 7 (FIG. 7 shows a graph of VAS of energy with BKP administration), and Table 5 and FIG. 8 (FIG. 8 shows a graph of VAS of focus with BKP administration).

TABLE 1

Blood glucose levels (mg/dL) following BHP and BKP administration.

| | Time points: | | | | | |
|---|---|---|---|---|---|---|
| | 0 min. | 30 min. | 60 min. | 90 min. | 120 min. | 150 min. |
| | Subject 1 | | | | | |
| BHP | 84 | 85 | 75 | 79 | 86 | 91 |
| BKP | 88 | 84 | 79 | 83 | 85 | 87 |
| | Subject 2 | | | | | |

TABLE 1-continued

Blood glucose levels (mg/dL) following BHP and BKP administration.

| | \multicolumn{6}{c}{Time points:} | | | | | |
|---|---|---|---|---|---|---|
| | 0 min. | 30 min. | 60 min. | 90 min. | 120 min. | 150 min. |
| BHP | 84 | 76 | 66 | 79 | 81 | 90 |
| BKP | 91 | 91 | 83 | 76 | 90 | 81 |
| | | | Combined | | | |
| BHP | 84 | 80.5 | 70.5 | 79 | 83.5 | 90.5 |
| BKP | 89.5 | 87.5 | 81 | 79.5 | 87.5 | 84 |

TABLE 2

Blood ketone levels (mMol) following BHP and BKP administration.

| | 0 min. | 30 min. | 60 min. | 90 min. | 120 min. | 150 min. |
|---|---|---|---|---|---|---|
| | | | Subject 1 | | | |
| BHP | 0.1 | 1.8 | 0.7 | 0.2 | 0.2 | 0.2 |
| BKP | 0.1 | 0.1 | 0.2 | 0.1 | 0.1 | 0.1 |
| | | | Subject 2 | | | |
| BHP | 0.1 | 1.4 | 0.4 | 0.2 | 0.4 | 0.2 |
| BKP | 0.1 | 0.1 | 0.2 | 0.1 | 0.1 | 0.1 |
| | | | Combined | | | |
| BHP | 0.1 | 1.6 | 0.55 | 0.2 | 0.3 | 0.2 |
| BKP | 0.1 | 0.1 | 0.2 | 0.1 | 0.1 | 0.1 |

TABLE 3

VAS of Well-Being following BHP and BKP administration.

| | 0 min. | 30 min. | 60 min. | 90 min. | 120 min. | 150 min. |
|---|---|---|---|---|---|---|
| | | | Subject 1 | | | |
| BHP | 7 | 5 | 5 | 7 | 5 | 6 |
| BKP | 7 | 7 | 9 | 9 | 9 | 9 |
| | | | Subject 2 | | | |
| BHP | 5 | 5 | 4 | 5 | 4 | 4 |
| BKP | 6 | 6 | 6 | 6 | 7 | 7 |
| | | | Combined | | | |
| BHP | 6 | 5 | 4.5 | 6 | 4.5 | 5 |
| BKP | 6.5 | 6.5 | 7.5 | 7.5 | 8 | 8 |

TABLE 4

VAS of Energy following BHP and BKP administration.

| | 0 min. | 30 min. | 60 min. | 90 min. | 120 min. | 150 min. |
|---|---|---|---|---|---|---|
| | | | Subject 1 | | | |
| BHP | 5 | 4 | 5 | 7 | 5 | 7 |
| BKP | 7 | 7 | 7 | 8 | 8 | 9 |
| | | | Subject 2 | | | |
| BHP | 3 | 3 | 2 | 3 | 4 | 5 |
| BKP | 5 | 6 | 7 | 6 | 7 | 7 |
| | | | Combined | | | |
| BHP | 4 | 3.5 | 3.5 | 5 | 4.5 | 6 |
| BKP | 6 | 6.5 | 7 | 7 | 7.5 | 8 |

TABLE 5

VAS of Focus following BHP and BKP administration.

| | 0 min. | 30 min. | 60 min. | 90 min. | 120 min. | 150 min. |
|---|---|---|---|---|---|---|
| | | | Subject 1 | | | |
| BHP | 5 | 5 | 5 | 5 | 5 | 5 |
| BKP | 6 | 5 | 7 | 7 | 7 | 8 |
| | | | Subject 2 | | | |
| BHP | 2 | 3 | 3 | 3 | 5 | 5 |
| BKP | 5 | 6 | 5 | 6 | 7 | 6 |
| | | | Combined | | | |
| BHP | 3.5 | 4 | 4 | 4 | 5 | 5 |
| BKP | 5.5 | 5.5 | 6 | 6.5 | 7 | 7 |

Example 2: C5-Ketone Administration as a Method to Lower Exertion During Exercise The purpose of this experiment was to see if C5 ketones could lower exertion during moderate and high intensity cycling exercise. Five (5) college aged males were given a placebo or BKP (10 grams) prior to and during 2 minute low, moderate and high intensity cycling bouts. BKP is able to lower perceived exertion at both moderate and high intensity exercise compared to a placebo. See Table 6, which shows the Borg Rating of Perceived Exertion (RPE), which is a way of measuring physical activity intensity level. Perceived exertion is how hard one feels like the body is working.

TABLE 6

Rating of Perceived Exertion (RPE)

| | Baseline | Low Intensity | Moderate Intensity | High Intensity | 30 min-Post |
|---|---|---|---|---|---|
| BKP | 7 ± 1 | 9 ± 1 | 13 ± 2 | 17 ± 2 | 8 ± 1 |
| Placebo | 7 ± 1 | 9 ± 1 | 14 ± 2 | 18 ± 1 | 9 ± 1 |

Discussion

The results of these findings show that C5 ketone bodies lower blood glucose, increase blood ketone levels, and increase visual analog scales of well-being, focus, and energy in otherwise healthy males. The disclosure further shows that C5 ketones are able to lower perceived exertion at both moderate and high intensity exercise. This disclosure has significant implications ranging from therapeutic effects to cognitive and athletic performance in a wide array of populations.

What is claimed is:

1. A method for aiding in at least one of weight loss or fat loss in an individual, the method comprising:
    administering a composition to the individual, wherein the composition comprises 1 to 50 g of β-hydroxypentanoate or a salt thereof, and
    wherein administration of the composition aids in at least one of weight loss and/or fat loss in the subject individual.

2. The method of claim 1 wherein the composition further comprises β-ketopentanoate or salt thereof.

3. The method of claim 1 wherein the β-hydroxypentanoate or salt thereof in the composition comprises about 1 to about 20 of β-hydroxypentanoate or salt thereof.

4. The method of claim 1 wherein the composition further comprises at least one other carbon length ketone that is not a C5-ketone.

5. The method of claim 1 wherein the composition further comprises is a C4-ketone.

6. The method of claim 1 wherein administration of the composition decreases blood glucose levels in the individual.

7. The method of claim 1 wherein the composition is formulated as a controlled release formulation or a sustained release formulation.

8. A method for increasing blood ketone levels in an individual, the method comprising:
    orally administering a composition comprising about 1 g to about 50 g of at least one of:
    β-hydroxypentanoate,
    β-hydroxypentanoate salt,
    β-ketopentanoate,
    or β-ketopentanoate salt;
    wherein the composition is administered orally to increase blood ketone levels in the subject.

9. A method for aiding in at least one of weight loss or fat loss in an individual, the method comprising:
    orally administering a composition comprising about 1 g to about 50 g of β-ketopentanoate or a salt thereof;
    wherein oral administration of the composition aids in at least one of weight loss or fat loss.

10. A composition for at least one of aiding in weight loss, aiding in fat loss, or increasing blood ketone levels in an individual, the composition consisting essentially of:
    about 1 g to about 20 g of a C5-ketone or salt thereof, wherein the C5 ketone or salt thereof comprises at least one of β-hydroxypentanoate or β-ketopentanoate, and
    optionally, at least one of:
        one or more pharmaceutical carriers,
        one or more pharmaceutical excipients,
        one or more emulsifying agents,
        one or more wetting agents,
        one or more suspending agents,
        one or more diluting agents,
        one or more buffering agents,
        or one or more release rate impacting agents;
    wherein oral administration of the composition aids in at least one of weight loss, aids in fat loss, or increases blood ketone levels in the individual.

11. The method of claim 10 wherein the β-hydroxypentanoate in the composition comprises at least one of a sodium β-hydroxypentanoate salt, calcium β-hydroxypentanoate salt, or magnesium β-hydroxypentanoate salt.

12. The method of claim 1, wherein administering the composition at least one of increases mental performance levels, or increases physical performance levels, or lowers exertion during exercise in the individual.

13. The method of claim 1 wherein the β-hydroxypentanoate comprises at least one of a sodium β-hydroxypentanoate salt, calcium β-hydroxypentanoate salt, or magnesium β-hydroxypentanoate.

14. The method of claim 1 wherein the β-hydroxypentanoate in the composition comprises β-hydroxypentanoate salts.

15. The method of claim 9 wherein administration of the composition increases blood glucose levels.

16. The method of claim 9 wherein the β-hydroxypentanoate comprises at least one of a sodium β-hydroxypentanoate salt, calcium β-hydroxypentanoate salt, or magnesium β-hydroxypentanoate.

17. The method of claim 9, wherein the β-ketopentanoate comprises at least one of a sodium β-ketopentanoate salt, calcium β-ketopentanoate salt, or magnesium β-ketopentanoate salt.

18. The method of claim 10 wherein the β-ketopentanoate in the composition comprises at least one of a sodium β-ketopentanoate salt, calcium β-ketopentanoate salt, or magnesium β-ketopentanoate salt.

19. The method of claim 10 wherein the β-hydroxypentanoate consists essentially of R-β-hydroxypentanoate.

20. The method of claim 10 wherein the β-hydroxypentanoate consists essentially of L-β-hydroxypentanoate.

* * * * *

UNITED STATES PATENT AND TRADEMARK OFFICE
CERTIFICATE OF CORRECTION

| | |
|---|---|
| PATENT NO. | : 11,337,945 B2 |
| APPLICATION NO. | : 16/306412 |
| DATED | : May 24, 2022 |
| INVENTOR(S) | : Ryan P. Lowery et al. |

It is certified that error appears in the above-identified patent and that said Letters Patent is hereby corrected as shown below:

In the Claims

At Column 13, Claim 1, Line 13, the words "one of weight loss and/or fat loss in the subject individual" should read --one of weight loss or fat loss in the individual--.

At Column 13, Claim 5, Line 24, the word "is" should be deleted.

Signed and Sealed this
Twenty-third Day of August, 2022

Katherine Kelly Vidal
*Director of the United States Patent and Trademark Office*